United States Patent
Köbel

(10) Patent No.: US 11,116,700 B2
(45) Date of Patent: Sep. 14, 2021

(54) PROCESS FOR THE GENERATIVE PRODUCTION OF DENTAL MOLDINGS

(71) Applicant: decema GmbH, Hilzingen (DE)

(72) Inventor: Stefan Köbel, Dachsen (CH)

(73) Assignee: decema GmbH, Hilzingen (DE)

(*) Notice: Subject to any disclaimer, the term of this patent is extended or adjusted under 35 U.S.C. 154(b) by 610 days.

(21) Appl. No.: 15/927,362

(22) Filed: Mar. 21, 2018

(65) Prior Publication Data

US 2018/0303723 A1    Oct. 25, 2018

(30) Foreign Application Priority Data

Mar. 21, 2017 (DE) ............... 10 2017 106 101.0

(51) Int. Cl.
| | | |
|---|---|---|
| *A61K 6/78* | (2020.01) | |
| *B33Y 80/00* | (2015.01) | |
| *B33Y 10/00* | (2015.01) | |
| *B29C 64/106* | (2017.01) | |
| *B28B 11/24* | (2006.01) | |
| *B33Y 30/00* | (2015.01) | |
| *B28B 1/00* | (2006.01) | |
| *B33Y 70/00* | (2020.01) | |
| *A61C 13/00* | (2006.01) | |
| *A61K 6/802* | (2020.01) | |
| *B29C 64/393* | (2017.01) | |
| *B22F 10/10* | (2021.01) | |
| *C04B 35/48* | (2006.01) | |
| *C04B 35/63* | (2006.01) | |
| *B22F 7/06* | (2006.01) | |
| *C09D 7/40* | (2018.01) | |
| *C04B 35/64* | (2006.01) | |

(52) U.S. Cl.
CPC .......... *A61K 6/78* (2020.01); *A61C 13/0013* (2013.01); *A61C 13/0019* (2013.01); *A61K 6/802* (2020.01); *B22F 10/10* (2021.01); *B28B 1/001* (2013.01); *B28B 11/243* (2013.01); *B29C 64/106* (2017.08); *B29C 64/393* (2017.08); *B33Y 10/00* (2014.12); *B33Y 30/00* (2014.12); *B33Y 70/00* (2014.12); *B33Y 80/00* (2014.12); *C04B 35/48* (2013.01); *C04B 35/63* (2013.01); *B22F 7/06* (2013.01); *B22F 2998/10* (2013.01); *C04B 35/64* (2013.01); *C09D 7/40* (2018.01); *C09D 7/70* (2018.01)

(58) Field of Classification Search
CPC ..... B29C 64/393; B29C 64/106; B33Y 10/00; B22F 3/008; C04B 35/48; C04B 35/63; C04B 35/64
See application file for complete search history.

(56) References Cited

U.S. PATENT DOCUMENTS

| | | | | |
|---|---|---|---|---|
| 5,697,043 A | * | 12/1997 | Baskaran | C04B 35/636 264/621 |
| 6,036,777 A | | 3/2000 | Sachs | |
| 6,322,728 B1 | | 11/2001 | Brodkin et al. | |
| 9,908,819 B1 | | 3/2018 | Kollenberg | |
| 2004/0262803 A1 | | 12/2004 | Neilsen et al. | |
| 2010/0020832 A1 | * | 1/2010 | Hoffman | H01S 3/109 372/5 |
| 2016/0100621 A1 | * | 4/2016 | Diaz | B29C 64/153 426/89 |
| 2016/0332373 A1 | | 11/2016 | Kuhn et al. | |
| 2017/0196666 A1 | * | 7/2017 | Bohm | A61K 6/818 |

FOREIGN PATENT DOCUMENTS

| | | |
|---|---|---|
| DE | 69025147 T2 | 9/1996 |
| DE | 102011117005 A1 | 4/2013 |
| WO | 2014067990 A1 | 5/2014 |
| WO | 2015168463 A1 | 11/2015 |
| WO | WO-2015177348 A1 * | 11/2015 ............ A61K 6/887 |

OTHER PUBLICATIONS

Extended European Search Report for the corresponding application EP18 163 176.3, 8 pages, dated Jul. 17, 2018.
Extended European Search Report for corresponding German application 10 2017 106 101.0, 17 pages, dated Jul. 17, 2018 (previously submitted on Mar. 18, 2020).
First Office Action for corresponding German application 10 2017 106 101.0, 10 pages, dated May 25, 2020.
Second Office Action for corresponding German application 10 2017 106 101.0, 11 pages, dated Dec. 9, 2020.

* cited by examiner

*Primary Examiner* — Michael M. Robinson

(74) *Attorney, Agent, or Firm* — Ohlandt, Greeley, Ruggiero & Perle, L.L.P.

(57) ABSTRACT

The invention relates to a method for generatively producing a dental molding for at least one of dental restoration and dental prostheses. The method comprises the following steps: a) providing at least one layer of a dispersion, particularly an aqueous dispersion, wherein the dispersion comprises at least one binder, and wherein the dispersion comprises ceramic particles and/or glass ceramic particles and/or powder metal particles; b) applying hardeners to the layer of dispersion in places for activating the at least one binder for hardening the layer of the dispersion in places, whereby a rough blank is obtained, particularly a green body, wherein at least two hardeners having different material composition from each other are used; and c) sintering the rough blank into the dental molding.

15 Claims, No Drawings

PROCESS FOR THE GENERATIVE PRODUCTION OF DENTAL MOLDINGS

CROSS REFERENCE TO RELATED APPLICATION

The present application claims foreign priority under 35 USC § 119 to German Patent Application No. DE 10 2017 106 101.0 filed on Mar. 21, 2017, the entirety of which is incorporated by reference hereby

TECHNICAL FIELD

The present invention relates to a method for generatively producing a dental molding, a dental molding produced by means of a generative production method, and a system for generatively producing a dental molding.

BACKGROUND ART

Additive production methods allow moldings made of ceramics and/or powder-metallurgical materials to be produced from three-dimensional computer models, such as CAD data, without requiring component-specific tooling. In additive manufacturing methods, layers of a dispersion and a hardener are applied alternately to a substrate. Printing methods and/or spraying methods are particularly used for applying the layers to the substrate. Effects of polymerization are used for hardening, for example. The repeated overlaid printing of the layers produces a rough blank as a three-dimensional object. Because the effort of producing castings is eliminated, additive manufacturing methods are particularly suitable for providing dental prosthetics, such as dental implants, inlays, crowns, and bridges.

In contrast to laser melting and binder jetting, where the raw material to be processed is applied to a substrate in powder form, an additive manufacturing method can be used for processing a greater selection of materials, because applying the material in powder form in a dispersion allows greater densities and greater homogeneity of the rough blank. In addition, unlike stereolithography, no monomers are needed, which present a health and environmental risk, and the total polymer content is significantly lower, facilitating subsequent debindering and firing processes of the component.

Previously known additive manufacturing methods have the disadvantage, however, that chemicals posing a health risk are often used for efficiently producing the desired rough blank, or dusts posing a health risk can occur. The provision of so-called gradient components, whose physical and/or chemical properties change throughout the volume of the component, is also very difficult and, in certain technical fields, impossible. In particular, no additive method for individually adapting physical and/or chemical properties along the rough blank is known.

A generative method for producing a ceramic green compact or molding is known from WO 2014/067990 A1. In particular, a hardening compound comprising an organic element compound, an organic binder, and a solvent or dispersing agent is applied to a ceramic, glass ceramic, or glass powder. The method reduces clogging of print heads and allows a substantially homogenous color picture. One disadvantage, however, is the relatively complex composition of the hardening compound.

WO 2015/168463 A1 discloses a method for producing dental prostheses. In a first step, a powder bed is provided, and in a second step a binder is selectively applied thereto. The steps are repeated multiple times until the desired green body has been produced. Finally, the part of the powder not exposed to the binder is removed and the green body is sintered. This method possesses the disadvantage that the powder bed requires relatively large grain size in the range of 10 micrometers. This leads to relatively large interstices between the individual grains, which can disadvantageously affect the sintering process and the physical and esthetic properties of the finished molding.

Publication DE 10 2011 117 A1 discloses a method for producing a ceramic molding, particularly in the form of a dental prostheses, on the basis of a generative production method. Individual slurry layers thereby have color pigments and a material compound for hardening the slurry layer each applied to selected areas. The green body is finally sintered to obtain a molding. One disadvantage of the method is the necessity for additionally providing color pigments for coloring the molding.

SUMMARY OF THE INVENTION

Based on the known prior art, it is an object of the present invention to provide an improved method for generatively producing a molding. In particular, the ability to adjust the coloring and other physical properties is improved. A further object is providing a molding for versatile use and produced by means of a generative production method, and a system for generatively producing such a molding.

The object is achieved by a method, a molding, and a system according to the independent claims. Advantageous refinements arise from the dependent claims, the description, and the embodiments. A method for generatively producing dental moldings for tooth restoration and/or as dental prostheses is disclosed accordingly. The method comprises the following steps: a) providing at least one layer of a dispersion, particularly an aqueous dispersion, wherein the dispersion comprises at least one binder, and wherein the dispersion comprises ceramic particles and/or glass ceramic particles and/or powder metal particles; b) applying hardeners to the layer of dispersion in places for activating the at least one binder for hardening the layer of the dispersion in places, whereby a rough blank is obtained, particularly a green body, wherein at least two hardeners having different material composition from each other are used; and c) sintering the rough blank into the dental molding.

The term hardener is understood to be a substance forming a three-dimensional network through a chemical reaction with a polymer (or monomer) exactly as is the case for two-component adhesives, for example, or for gelling (sol-gel transition) of polymers.

Hydrogel-forming polymers can be of natural or synthetic origin. Hydrogels are made of a three-dimensional polymer network stabilizing an aqueous phase. Hydrogels arise due to physical and/or chemical cross-linking. Chemically cross-linked hydrogels have covalent bonds (e.g., polyacryl amide, polyethylene glycol (PEG), hyaluronic acid, chitosan derivatives, etc.), while physically cross-linked hydrogels have transient, reversible compounds derived from the interactions between polymer chains, such as entanglement (e.g., polyvinyl alcohol, collagen, gelatins, many polysaccharides), ionic bonds (e.g., alginate, pectin, etc.) or hydrogen bonds. Hydrogels can also so be formed by modifying aqueous polymers, in that reactive groups are installed in the polymer and make the polymer chemically cross-linkable, or able to be excited to cross-linking by stimuli such as light, heat, or pH, or combinations thereof.

The method described herein for generatively producing a molding conceptually combines the advantages of stereolithography and binder jetting. The advantage of the method described herein is particularly the varying of the hardener. At least one of the hardeners can comprise additional components for dosing the rough blank during the printing process and thus imparting the final molding with additional properties. The use of different hardeners results in an additional degree of freedom in the production method with respect to the physical and/or chemical properties.

The hardeners can be provided particularly as a solution. For example, the hardeners each comprise de-ionized water, a saline solution, preferably a metal salt solution of no greater than 1 molarity, and additives. The additives can comprise cationic thinners, alcohols, and/or complexing agents. A droplet size when applying the hardener can be particularly reduced by means of rapidly evaporating alcohols. A reduction in droplet size enables improving local resolution in the production method and thus more precise adapting of the shape and/or properties of the rough blank or molding.

Ceramic color solids and/or other particles can also be included in the hardeners. At least one of the hardeners preferably comprises multivalent ions, particularly cations of transition metals. The ions can be selected according to the desired coloring of the molding and/or other physical and/or chemical properties to be achieved in the molding. The ions are zirconium ions, for example. For special desired colors, other ions can be included. Cobalt ions, for example, produce a blue color in aluminum oxide after sintering.

In method step a), the dispersion is preferably applied to a substrate, for example by spraying. The dispersion can be a binder dispersion or can comprise such a binder dispersion. For example, the dispersion comprises deionized water, ceramic raw materials, thinners, a polyelectrolyte such as alginate, for example, particularly ammonium alginate, and/or further additives such as glycerol and/or citric acid. The ceramic raw materials can comprise aluminum oxide ($Al_2O_3$), for example. The solids content of the dispersion is preferably at least 40 vol %, particularly preferably at least 50 vol %. The solids in the dispersion can be introduced into the dispersion in the form of a powder.

The binder can be any polymer capable of being cross-linked by ions to form a gel. Metal ions are preferably used for the cross-linking. The ions of multivalent cations are particularly preferred.

Ionotropic hydrogel-forming biopolymers, polyelectrolytes, and synthetic polymers can be used as binders. Such polymers are already known to the person skilled in the art.

Examples of such polymers capable of being cross-linked by means of multivalent ions are: polysaccharides, such as carrageenan, dextrin, gellan, scleroglucan, chitosan and derivatives thereof; water-soluble polyphosphazes such as poly(bis(4-carboxylphenoxy)phosphazes); polyacrylates; and polyamino acids.

In a preferred embodiment, the at least one binder and the ceramic particles and/or glass ceramic particles and/or powder metal particles are homogenously distributed in the dispersion.

The dispersion is equalized by means of a doctor blade, for example, and/or homogenously distributed on the substrate by means of vibrations. Vibrations, such as a back-and-forth motion, result in a homogenous and flat level of the dispersion on the substrate.

The hardeners can then be applied to the dispersion, for example using a printing procedure and/or by spraying. Due to diffusion, the active components of the hardeners, particularly ions present in the hardeners, penetrate into the dispersion and can lead to local gelation of the dispersion there. This corresponds approximately to the effect of radicals on monomers in stereolithography.

The method step a) is preferably repeated several times for producing the rough blank. For example, a first layer of the dispersion is first applied to the substrate. Hardeners are then applied to the first layer of the dispersion. A further layer of the dispersion, or a further dispersion different from the dispersion, can subsequently be applied to the hardened first layer. The further layer can then also be hardened using hardeners. As a final step, the dispersion is applied (known as "re-coating"). The composition of the hardeners, that is, the relative proportions thereof, can thereby be different for the hardening of the further layer than the composition of the hardeners used for hardening the first layer. By repeating the method step a), a rough blank (known as a green body) can thus be produced in layers.

In a further preferred embodiment of the method, a relative proportion of the hardeners to each other is controlled on the basis of position. The proportion of each hardener can particularly be adjusted as a function of position. The term "as a function of position" hereby and hereafter involves adjusting the relative proportion both in the horizontal or lateral direction and in the vertical direction, that is, in the direction of growth. The relative proportion of a hardener is hereby and hereafter the weight fraction or the volume fraction. Controlling the proportion as a function of position makes it possible to adjust physical and/or chemical properties of the molding as a function of position. Different regions of the molding can particularly be adapted to different areas of application.

According to at least one embodiment of the method, at least one of the hardeners comprises metal ions. The metal ions are preferably selected so that the hardener achieves additional functions, such as coloring, in addition to hardening. Because higher concentrations are often required for a desired coloring, in this case a part of the ions can be complexed in the hardener.

It is particularly possible that at least one of the hardeners comprises ions of a first type and/or of a second type. Ions of a further type, such as a third or fourth type, are also possible. Different hardeners can particularly comprise ions of different types and/or different compositions of the ions of different types. When "ions" are described hereby and hereafter, the ions of the first type, ions of the second type, and/or ions of a further type are understood. For example, homologous ions can be used as ions of different types.

According to at least one embodiment of the method, at least one of the hardeners comprises metal ions of a first type. The reaction temperature of the ions of the first type and the powder material is below a sintering temperature used during sintering in the method step c). The reaction temperature of any present ions of a second type and/or of a further type is also below the sintering temperature. The sintering temperature is at least 1832° F. (1000° C.), for example, and no greater than 3632° F. (2000° C.), preferably at least 2192° C. (1200° C.) and no greater than 2912° F. (1600° C.). It is thereby possible that the ions of the first type are not evaporated out of the rough blank by sintering. During sintering, the ions of the first type are freely displaceable within the crystal matrix of the rough blank. In other words, the ions of the first type dissolve at least partially in the crystal matrix of the rough blank as a solid solution during sintering. At least part of the ions of the first type can thereby be dissolved inside the rough blank.

Hereby and in general hereafter, the terms "ions of the first type", "ions of the second type", and "ions of a further type" apply to the chemical element fundamental to the ions, each potentially comprising or being one of the group of titanium, chromium, manganese, iron, cobalt, nickel, copper, zinc, aluminum, strontium, yttrium, zirconium, niobium, lanthanum, cerium, praseodymium, terbium, erbium, and ytterbium. The "ions of the first type", "ions of the second type", and "ions of a further type" each correspond to a different element of the aforementioned group.

According to at least one embodiment of the method, at least one of the hardeners comprises ions of at least one second type. The ions of the second type are at least partially dissolved in the crystal matrix of the rough blank as a solid solution during sintering in method step c). In other words, the ions of the second type are at least partially integrated in the crystal matrix of the rough blank and partially occupy lattice sites of the crystal matrix. In other words, the ions of the second type can act as a doping, whereby physical and/or chemical properties of the molding can be varied locally.

According to at least one embodiment of the method, the sintering temperature used for sintering in method step c) is reduced by the ions of the second type. In other words, the sintering requires a lower sintering temperature due to the ions of the second type. The required sintering temperature can particularly be proportional to the solidus temperature of the material of the rough blank. By integrating the ions of the second type into the crystal matrix of the rough blank during the sintering process, the crystal structure can be modified at least locally and the sintering temperature can be reduced. Hereby and hereafter, the "crystal structure" is particularly the crystal matrix of the rough blank present as a ceramic, glass ceramic, and/or powdered metal.

According to at least one alternative or additional embodiment of the method, the ions of the second type locally modify at least one physical property and/or at least one chemical property of the sintered molding. The adaption of the physical and/or chemical properties can be based particularly on a local change to the crystal structure due to the ions of the second type. Local changes can be differentiated from global changes in that only a partial region of the crystal structure of the rough blank is varied. For example, the lattice spacing and/or the bond energy of the crystal structure are modified by the ions of the second type.

The physical property is preferably an optical property of the molding. The chemical property is further preferably a catalytic properly of the molding. Optical properties of the molding are, for example, the color, transparency, opacity, and/or refractive index thereof. The change to the optical property can result from integrating optically active ions in the crystal structure of the rough blank and/or from an at least local change in the band gap of the crystal matrix of the molding.

According to at least one embodiment of the method, at least one of the hardeners comprises ions. The ions can be the ions of the first type, the ions of the second type, and/or optionally present ions of a further type. The ions, particularly the ions of the first type and/or the ions of the second type, form precipitations in the structure of the crystal structure of the rough blank during sintering in method step c). The molding produced from the rough blank can then comprise an anisotropic structure, particularly a two-phase structure, arising during sintering. It is particularly possible to control the position of the precipitations by selecting the ions and/or the position of the ions prior to sintering and thus to vary a proportion of the ions locally along the rough blank.

According to at least one embodiment of the method, the ions of the at least one hardener, particularly the ions of the first type and/or the ions of the second type, are cations having a valence of at least three. The cations can thus be particularly trivalent or of higher valence, such as tetravalent, for example.

According to at least one embodiment of the metal, the dispersion comprises ceramic and/or glass ceramic and/or metal materials in powder form. At least one of the hardeners at least partially comprises cations in dissolved form and as components of the solid material in powder form in the dispersion. In other words, the dispersion and at least one of the hardeners comprise cations of the same type. The cations are particularly the ions of the first type, the ions of the second type, and/or the ions of a further type. The use of the same cations for the hardener and the material in powder form makes it possible to keep nearly constant the physical and/or chemical properties of the base material, that is, the ceramic and/or glass ceramic and/or metal materials in powder form. It is thus possible to avoid unnecessarily contaminating highly pure base materials.

In a preferred embodiment, the dispersion comprises at least one polysaccharide and/or at least one hydrocolloid in the form of an alginate, particularly an ammonium alginate. The properties of the dispersion can be specifically influenced as a function of the selected alginate. In addition, dispersions comprising two different alginates can also be used. The rheological properties and gel forming can thereby be particularly specifically influenced.

In a further preferred embodiment, the dispersion comprises at least one polyacrylate. A broad range of polyacrylates are available commercially. The specific selection of a polyacrylate accordingly results in a relatively greater range for potential influencing the viscosity of the dispersion and the gel properties thereof. Pure polyacrylic acids can be used as the polyacrylate, for example. SYNTRAN® polyacrylates, particularly such as SYNTRAN®8220, SYNTRAN®8550-N, and SYNTRAN®8740, can be used.

In addition, advantageous properties of the dispersion can also be achieved by a combination of alginate and polyacrylate. The reaction kinetics of the dispersion can thereby be particularly influenced. For example, a lower viscosity of the dispersion with unchanged gelling strength can be achieved in this manner.

Alternatively, the dispersion can also comprise a natural or synthetic polyelectrolyte and/or at least one polysaccharide and/or at least one hydrocolloid from the group of pectin, galactomannan, carrageenan, dextran, gellan, scleroglucan, chitosan, aqueous polyphosphazes such as poly(bis (4-Carboxyphenoxy)phosphaze), and polyamino acids.

The use of polyelectrolytes, polysaccharides, and/or hydrocolloids can generally be considered safe from a health standpoint. These materials can also be provided easily and at low cost. The combination of differently doped and/or compounded polyelectrolytes, polysaccharides, and/or hydrocolloids can be used for adjusting the physical and/or chemical properties of the dispersion and of the rough blank. Adding a polyelectrolyte or polysaccharide or hydrocolloid thus causes a change in the rheological properties of the dispersion, and the properties of the rough blank change with the type and amount of the polyelectrolyte or polysaccharide or hydrocolloid.

According to a preferred refinement, the dispersion comprises at least two different polyacrylates. A potentially low viscosity of the dispersion and highest possible strength of the rough blank produced therefrom can thereby be achieved.

A molding is also disclosed. The molding can preferably be produced by means of a generative production method and particularly preferably by means of the method described here. That is, all features disclosed for the method are also disclosed for the molding, and vice versa.

The molding is preferably implemented as a dental prosthesis. The molding is particularly implemented as a bridge, as a bridge framework, as an inlay, as an only, as a crown, as an implant, as an abutment, and/or as a veneer. The molding comprises a ceramic, a glass ceramic, and/or a powdered metal or is made of a combination of these materials. A physical property and/or a chemical properly of the molding varies locally. In other words, the molding comprises different physical and/or chemical properties in different regions along the volume of the molding. The color of the molding can vary locally, for example.

A system for generatively producing a molding is also disclosed. The system is preferably set up for performing a method for producing a molding, particularly a molding described here. That is, all features disclosed for the method and the molding are also disclosed for the system, and vice versa.

The system for generatively producing a molding accordingly comprises a dispenser and/or a printer for applying a dispersion and a plurality of different hardeners. The dispersion comprises at least one binder. The dispersion further comprises ceramic particles and/or glass ceramic particles and/or powder metal particles. The printer is preferably set up for adjusting the amount of each of the different hardeners as a function of position. A relative proportion of the hardeners to each other can then be controlled by means of the printer as a function of position.

According to a preferred embodiment, the system comprises at least the dispersion and furthermore at least two different hardeners. The different hardeners can comprise ions of a different type, for example, such as ions of a first type and ions of a second type, in different proportions.

DETAILED DESCRIPTION OF PREFERRED EMBODIMENTS

The following describes in greater detail an exemplary embodiment of a method described herein for generatively producing a molding and a system described herein for generatively producing a molding.

In a first method step, a layer of a dispersion is applied to a substrate. In a second method step, hardeners are applied to the layer of the dispersion. In the present embodiment, a hardener of a first type and a hardener of a second type are used. For example, the hardener of the first type comprises a different material composition, particularly ions of a different type, than the hardener of the second type. The hardener of the first type can comprise titanium and the hardener of the second type can comprise chromium, for example. Alternatively, the hardeners of the first and second type can each comprise manganese, iron, cobalt, nickel, copper, zinc, aluminum, strontium, yttrium, zirconium, niobium, lanthanum, cerium, praseodymium, terbium, erbium, or ytterbium. The different types of hardener can be selected according to the desired coloring and/or other physical and/or chemical properties of the rough blank to be produced.

The dispersion can comprise aluminum oxide as a raw material, such as calcinated aluminum oxide from the Baikowski company (HP DBM). The dispersion can also comprise alginate. For providing the dispersions, an aluminum oxide suspension (for example having 56 vol % aluminum oxide) and an alginate solution (for example having 2-3 wt % alginate) can be prepared 24 hours prior to using the dispersion in the method. The aluminum oxide suspension and the alginate solution can be combined for producing the dispersion. The alginate concentration in the final dispersion is 0.4-0.75 wt %, for example, typically 0.5 wt %. The dispersion can further comprise 0.1 wt % ammonium citrate. The layer of the dispersion, the hardener of the first type, and the hardener of the second type are applied by means of a system comprising a dispenser and a printer. The dispenser comprises the material of the dispersion and is set up for applying the dispersion to the substrate or to layers of the dispersion applied in preceding method steps.

According to one embodiment, the substrate can be lowered after each application step. The lowering results in the dispersion being replenished from the dispenser, wherein the dispersion flows over the rough blank while the same is immersed in the dispersion by the lowered height. Alternatively, the dispenser can be provided in the form of a print head applying the dispersion to the substrate or to the rough blank.

The printer is set up for printing an adjustable amount of the hardener of the first type and/or the hardener of the second type to the layer of the dispersion. The printer can comprise different regions to this end, such as cartridges in which the hardener of the first type and the hardener of the second type are loaded.

The droplet size provided by the printer is 10 pl, for example, whereby the positioning of the individual hardener can be adjusted precisely. For example, a layer thickness of the hardener of the first type and/or of the hardener of the second type comprises 10 μm if a layer thickness of the layer of the dispersion is 100 μm. This corresponds to an amount of hardener of the first and/or second type of substantially less than 1 μl/cm$^2$ of the layer of the dispersion, for example.

The method steps described herebefore are repeated several times, whereby a rough blank can be provided. The rough blank comprises a plurality of layers of the dispersion, between each of which layers of the hardener of the first type disposed of the hardener of the second type are disposed (also referred to as "layer stack" hereafter). The amount of each of the hardener of the first type and the hardener of the second type has been modified as a function of position in the different layers by means of the printer, whereby the relative proportion of the hardener of the first type to the hardener of the second type can vary laterally along the layers (XY plane) and vertically along the layer stack (Z direction).

To increase the strength of the rough blank, the same can first be flushed after being produced, for example with water, and then treated with a saline solution. The rough blank can thereby be further reinforced.

In a further method step, the rough blank can be dried and debinded. For debinding (also referred to as debindering), the rough blank is subjected to a chemical treatment and/or a heat treatment, whereby any binders present, for example present in the dispersion, the hardener of the first type, and/or the hardener of the second type, are removed from the rough blank. The binders are pyrolyzed, gasified, or burned by the debinding. Drying and debinding can take place in a common method step, for example.

The rough blank is then sintered. The sintering of a rough blank produced from aluminum oxide ($Al_2O_3$) of the type Baikowski HP DBM, for example, can take place at a sintering temperature of 2912° F. (1600° C.). For example, the rough blank is sintered for one hour at a heating rate of 50° F./min (10° C./min). A molding having a density of at least 3.8 g/cm³ to no greater than 4.0 g/cm³, preferably at least 3.90 g/cm³ and no greater than 3.98 g/cm³, can thereby be provided. The density of the molding preferably corresponds to the sintering density achieved by sintering. Using the sintering parameters, it is possible to provide a molding having a flexural rigidity of 440 MPa, corresponding to the ISO standard 6872. Shrinkage of the rough blank during sintering is at least 15% and no greater than 30% in each spatial direction, for example. Lateral linear shrinkage can particularly be 18% and vertical shrinkage can be 21%. In order to accommodate the rough blank shrinking when sintering, the rough blank can be provided having greater dimensions.

A molding is preferably produced by means of the method described here before. The molding comprises first regions, second regions, and third regions, each comprising different concentrations or relative proportions of the material of the dispersion, the hardener of the first type, and/or the hardener of the second type. The second regions and the third regions can comprise a higher concentration of the hardener of the first type or the hardener of the second type than the first regions. The first regions, the second regions, and the third regions can arise from setting the relative ratios of the hardener of the first type and the hardener of the second type as a function of position. The hardener of the first type and/or the hardener of the second type can diffuse within the rough blank and form precipitations, whereby the different regions arise.

The molding comprises different physical and/or chemical properties in the different regions. For example, an optical property of the molding in the first region is different from an optical property of the molding in the second region and/or in the third region. Potential optical properties include, for example, the transparency, the color, and/or the opacity of the molding. Particularly if the molding is a dental prosthesis, the use of different hardeners influencing the optical properties in different manners can be used for copying the natural variation in tooth color, whereby the dental prosthesis can be provided with a natural appearance.

The invention is not limited to the embodiments by the description of the same. Rather, the invention comprises each new feature and each combination of features, particularly including each combination of features in the claims, even if the feature or the combination itself is not explicitly disclosed in the claims or the embodiments.

The invention claimed is:

1. A method for generatively producing a dental molding for at least one of a dental restoration and a dental prostheses, comprising:
   a) providing at least one layer of an aqueous dispersion, the dispersion comprising at least one binder, and the dispersion comprising at least one of ceramic particles, glass ceramic particles, and powder metal particles;
   b) applying a plurality of hardeners in places to the layer of the dispersion for activating the at least one binder for hardening the layer of the dispersion in places, whereby a rough blank is obtained, the rough blank being a green body, wherein at least one of the hardeners comprises ions of at least a first type, wherein at least two of the hardeners have different material compositions from each other being used, and wherein a relative proportion of the hardeners to each other is varied as a function of position within the dental molding; and
   c) sintering the rough blank into the dental molding.

2. The method according to claim 1, wherein the at least one binder and at least one of the ceramic particles, the glass ceramic particles, and the powder metal particles are homogenously distributed in the dispersion.

3. The method according to claim 1, wherein at least one of the hardeners comprises ions of at least a second type, wherein the ions of the second type are at least partially dissolved in a solid solution in the crystal matrix of the rough blank during sintering in step c), and the ions of the second type locally modify at least one of a physical property and a chemical property of the rough blank.

4. The method according to claim 3, wherein the at least one physical property is an optical property of the molding.

5. The method according to claim 3, wherein the at least one chemical property is a catalytic property of the molding.

6. The method according to claim 1, wherein at least one of the hardeners comprises ions of at least one second type, wherein the ions of the second type are at least partially dissolved in a solid solution in the crystal matrix of the rough blank during sintering in step c), and the sintering temperature used for sintering in step c) is reduced by the ions of the second type.

7. The method according to claim 1, wherein at least one of the hardeners comprises at least one of the ions of the first type and an ion of a second type, wherein the ions of the first type and the ions of the second type form precipitants in the structure of a crystal structure of the rough blank during sintering in step c).

8. The method according to claim 7, wherein the ions of the first type and the ions of the second type are cations having a valence of at least three.

9. A method for generatively producing a dental molding for at least one of a dental restoration and a dental prostheses, comprising:
   a) providing at least one layer of an aqueous dispersion, the dispersion comprising at least one binder, and the dispersion comprising at least one of ceramic particles, glass ceramic particles, and powder metal particles;
   b) applying a plurality of hardeners in places to the layer of the dispersion for activating the at least one binder for hardening the layer of the dispersion in places, whereby a rough blank is obtained, the rough blank being a green body, wherein at least two of the hardeners have different material compositions from each other being used, and wherein a relative proportion of the hardeners to each other is varied as a function of position within the dental molding; and
   c) sintering the rough blank into the dental molding, wherein the dispersion comprises at least one of ceramic, glass ceramic, and metal materials in powder form, wherein at least one of the hardeners also comprises cations at least partially in dissolved form as the cations are also a component of the solid material in powder form in the dispersion.

10. A method for generatively producing a dental molding for at least one of a dental restoration and a dental prostheses, comprising:
    a) providing at least one layer of an aqueous dispersion, the dispersion comprising at least one binder, and the dispersion comprising at least one of ceramic particles, glass ceramic particles, and powder metal particles;
    b) applying a plurality of hardeners in places to the layer of the dispersion for activating the at least one binder for hardening the layer of the dispersion in places, whereby a rough blank is obtained, the rough blank being a green body, wherein at least two of the hardeners have different material compositions from each other being used, and wherein a relative proportion of the hardeners to each other is varied as a function of position within the dental molding; and c) sintering the rough blank into the dental molding, wherein the dispersion comprises at least one of a polysaccharide and a hydrocolloid in the form of an ammonium alginate.

11. The method according to claim 1, wherein the dispersion comprises at least one polyacrylate.

12. The method according to claim 11, wherein the dispersion comprises at least two different polyacrylates.

13. The method according to claim 1, wherein the dental molding is implemented as at least one of a dental prosthesis, a bridge, a bridge frame, an inlay, an onlay, a crown, an implant, an abutment, and a veneer, and comprises at least one of a ceramic, a glass ceramic, and a metal, wherein at least one of a physical property and a chemical property of the molding varies locally.

14. The method for generatively producing the dental molding according to claim 13, further comprising providing at least one of a dispenser and a printer for applying the dispersion and the plurality of different hardeners.

15. The method according to claim 14, further comprising: providing the at least two different hardeners.

* * * * *